United States Patent [19]
Knoepfler

[11] Patent Number: 5,454,819
[45] Date of Patent: Oct. 3, 1995

[54] SPRING BIASED LAPAROSCOPIC SURGICAL NEEDLE HOLDER

[75] Inventor: Dennis J. Knoepfler, Amelia, Ohio

[73] Assignee: NuSurg Medical, Inc., Cincinnati, Ohio

[21] Appl. No.: 186,498

[22] Filed: Mar. 17, 1994

[51] Int. Cl.$^6$ .................................................. A61G 17/04
[52] U.S. Cl. ............................................................ 606/147
[58] Field of Search ...................................... 606/147–148, 606/205–207

[56] References Cited

U.S. PATENT DOCUMENTS

| | | |
|---|---|---|
| 984,756 | 2/1911 | Frisch . |
| 1,837,277 | 12/1931 | Lund . |
| 1,988,219 | 1/1935 | Segal . |
| 4,258,716 | 3/1981 | Sutherland . |
| 4,726,367 | 2/1988 | Shoemaker ............................... 128/303 |
| 4,898,157 | 2/1990 | Messroghli et al. ..................... 606/147 |
| 4,955,887 | 9/1990 | Zirm ........................................ 606/107 |
| 5,015,250 | 5/1991 | Foster ...................................... 606/147 |
| 5,171,250 | 12/1992 | Yoon ....................................... 606/142 |
| 5,176,699 | 1/1993 | Markham ............................... 606/206 |

OTHER PUBLICATIONS

Jaret Instrument Update (Mar. 1992), New Jarit Appel Laparoscopic Needle Holder, pp. 132–138.

Primary Examiner—Gary Jackson
Attorney, Agent, or Firm—Wood, Herron & Evans

[57] ABSTRACT

A surgical needle holder particularly adapted for use in laparoscopic procedures include a first and a second jaw element which have parallel engaging jaw faces. The first jaw element is stationary relative to the needle holder and the second jaw element is moveable. A rod extends from the moveable jaw element through the body of the needle holder and is spring biased forcing the moveable jaw element into engagement with the stationary jaw element. The jaw elements are opened by the handle which includes a generally V-shaped linkage between two handle members. When the handle members are squeezed together, the linkage is compressed and forced against the spring elements forcing it into compression and opening the jaw elements. Preferably the faces of the jaw elements are at a 30° angle relative to the axis. This allows a needle to be held in the jaws and inserted through the cannula in a laparoscopic procedure.

11 Claims, 2 Drawing Sheets

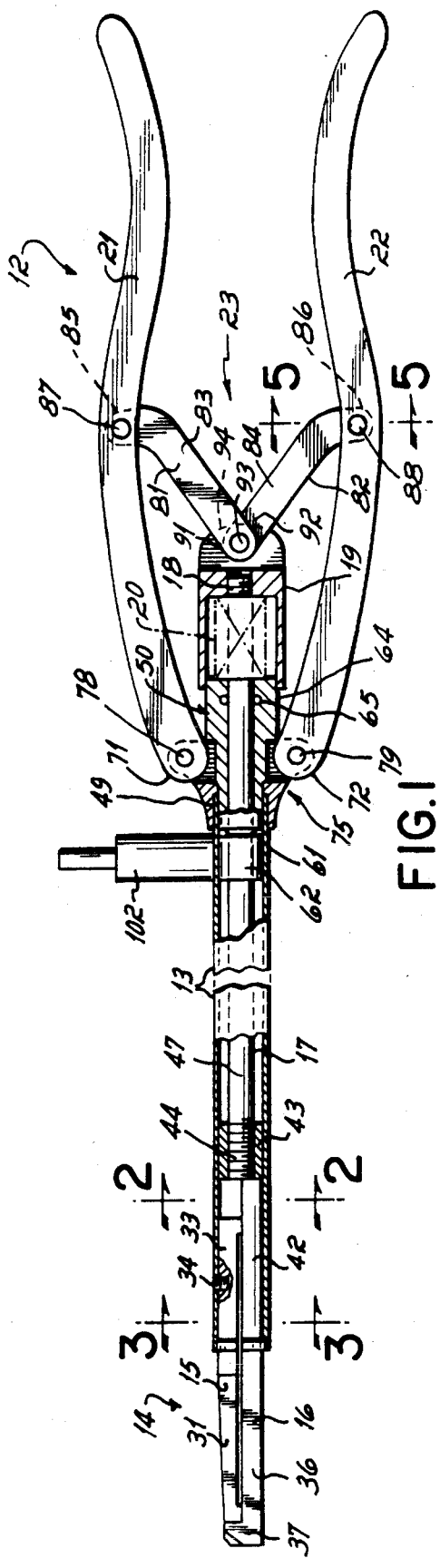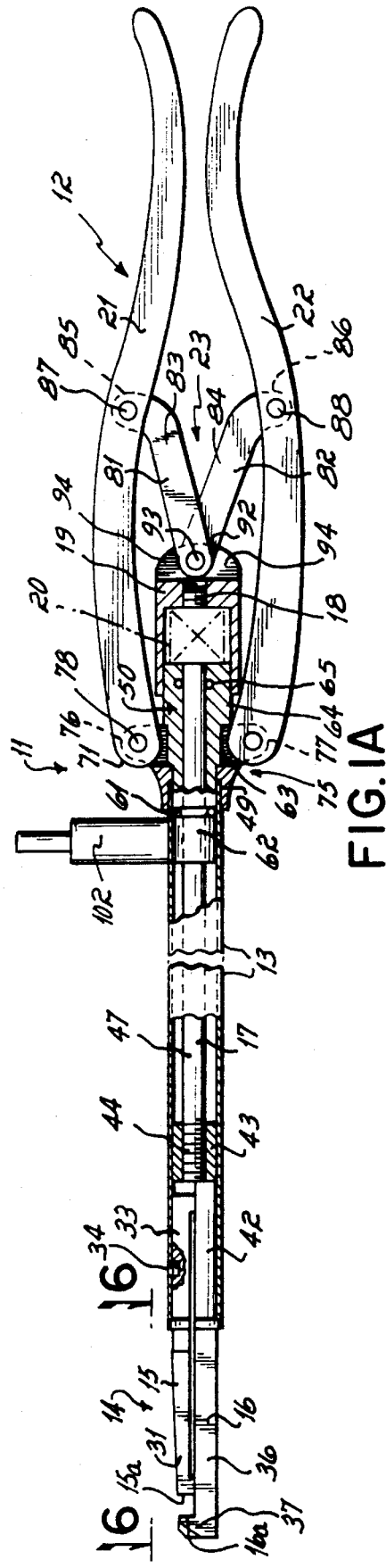

5,454,819

SPRING BIASED LAPAROSCOPIC SURGICAL NEEDLE HOLDER

BACKGROUND OF THE INVENTION

Scopic procedures are increasingly employed by surgeons to perform relatively major surgery. This permits access to an internal operative site through relatively narrow incisions. Incisions are made, and small tubes referred to as cannulas are inserted providing a passageway to the operative site.

As with most operative procedures, a certain degree of suturing is required. The needle with the thread attached must be placed at the operative site, grasped and manipulated about the operative site to provide the sutures. Such devices must include needle grasping elements, a handle, and a narrow shaft that permits the needle grasping elements to be inside the patient while the handle remains outside the patients.

The needle must be grasped firmly by the needle holder without the needle slipping or rotating during use. Prior needle holders have employed jaw elements which pivot together. With such devices, only a very small portion of the jaw face actually engages the needle. The needle can easily rotate relative to the jaw face.

Further, these needle holders frequently require the surgeon to maintain pressure on the needle holder at all times while the needle is being held. Some include a locking mechanism which must be released. Also, most pivot-jawed needle holders hold the needle in the arc of a curved needle which is not as secure as gripping on the flat plane of the needle.

One needle holder used for laparoscopic procedures is disclosed in U.S. Pat. No. 5,015,250. The disclosed needle holder uses a tube within a tube to hold a needle. The outer tube is notched so that edges of the tubes can contact the needle. This requires an excessively strong spring to hold the needle. Accordingly, it is very tiring. Although it discloses angled jaws, the angled jaws do not permit a needle to be grasped and inserted through a trocar designed for the needle holder.

This can be a particular problem with scopic procedures. The cannula or trocar generally has an internal diameter equal to the external diameter of the needle holder in order to maintain an airtight seal in the operative site. This is required because the operative site is inflated with gas to create a cavity which facilitates viewing of the procedure.

The needle, which is longer than the internal diameter of the cannula, cannot be placed into position by the needle holder. There simply is not enough room to fit the needle through the cannula while grasped by the needle holder. In order to overcome this, special devices have been designed to insert the needle into the operative site. These devices are then removed from the cannula and the needle holder placed in through the cannula.

SUMMARY OF THE INVENTION

Accordingly, it is an object of the present invention to provide a needle holder specially adapted for laparoscopic procedures.

Further, it is an object of the present invention to provide such a needle holder which permits the needle to be held by the needle holder and inserted through the cannula.

Further, it is an object of the present invention to provide such a needle holder wherein a maximum portion of the jaw face surface engages the needle.

It is also an object of the present invention to provide such a needle holder wherein the jaw faces are biased shut so that the surgeon does not have to press down on the handles of the needle holder except to release the needle.

The objects and advantages of the present invention are realized by a needle holder wherein there is a first and second jaw element, one being stationary and one moveable in an axial direction. Both jaw elements have engagable jaw faces that are parallel to each other at all times so that a large portion of the face engages the flat surface of the needle when closed.

The moveable jaw element is attached to a rod which is in turn attached to a spring held in compression. The spring forces the jaw elements closed so that in use, the jaw faces would be engaging the needle without the surgeon's hand pressing against the handles. The handles are connected to a V-shaped linkage which when compressed presses against the spring putting it further in compression and opening the jaw faces.

In a preferred embodiment, the jaw faces lie at an angle about 60° from the axis of the needle holder. The head of the needle holder is smaller than the shaft so that an arcuate needle with thread attached can be grasped by the needle holder and inserted through the cannula.

The objects and advantages of the present invention will be further appreciated in light of the detailed description and drawings.

BRIEF DESCRIPTION OF THE DRAWINGS

FIG. 1 is a plan view of the present invention, partially broken away, with the handles in a relaxed position;

FIG. 1A is a plan view of the present invention, partially broken away, with the handles in a compressed position;

DETAILED DESCRIPTION OF THE DRAWINGS

Figure 2:
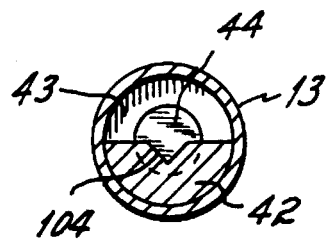
FIG. 2 is a cross-sectional view of FIG. 1 taken at lines 2—2.

As shown in FIGS. 1 and 2, the present invention is a needle holder 11 which has a handle mechanism 12, a cylindrical body 13, and a jaw pair 14. The jaw pair includes a fixed jaw 15, a moveable jaw 16 which is actuated relative to the fixed jaw by a central rod 17. The needle can be grasped between the knurled jaw faces 15a and 16a of the fixed and stationary jaws 15 and 16, respectively.

The proximal end 18 of rod 17 is screw fitted into a cap 19 which is biased by spring 20 to maintain the jaw faces in a closed position as shown in FIG. 1. The handle mechanism 12 acts to separate the jaw elements. The handle mechanism 12 includes a first handle element 21 and a second handle element 22 and a pivoted linkage 23 between the first and second handle elements 21 and 22. As shown in FIG. 1A, when the handle elements 21 and 22 are compressed relative to each other, cap 19 is forced against spring 20, forcing the rod forward 17, and opening the jaw faces.

More particularly, the fixed jaw element 15 includes a narrow forward portion 31 that terminates in jaw face 15a and semi-cylindrical rear portion 33. Portion 33 is fixed to the inside of the cylindrical body 13 by a flat-headed screw 34, although alternate means can be obviously used.

The moveable jaw element 16 includes head portion 37 which includes the inner jaw face 16a. The jaw element 16 also includes a narrow portion 36 which extends between the head portion 37 and a semi-cylindrical intermediate portion 42 which terminates in an internally threaded tubular portion 43. As shown, the distal end of the central rod 17 is externally threaded and screwed into the internal threaded portion 43 of the moveable jaw element 16, thus providing the connection. Rod 17 includes the distal, externally threaded portion 44 at one end and a smooth mid-section 47 followed by the proximal externally threaded portion 18 which again engages the cap 19. As shown, the cap 19, rod 17, and moveable jaw element 16 all move forward and rearwardly relative to the cylindrical body 13 as one unit.

The proximal end 49 of body 13 includes a plug 50. This plug 50 is a hollow cylindrical member having a stepped axial configuration. It includes an innermost narrow portion 62 which is slightly smaller in cross-sectional configuration than the internal diameter of body 13. An O-ring 61 located in a groove in this innermost portion 62 engages the interior surface of body 13 making the fluid tight seal. Mid-section 63 of the plug 50 has a cross-sectional diameter approximately equal to the exterior diameter of the tube 13, thus providing a continuous exterior surface. At the most upstream portion of this is an enlarged portion 64 or end portion which has a cross-sectional diameter slightly larger than the exterior of the surface of the tube 13. The end portion 64 of plug 50 includes an interior groove and an O-ring 65 which engages the rod 17 to provide a fluid tight seal between the interior and exterior of the needle holder.

Figure 5:
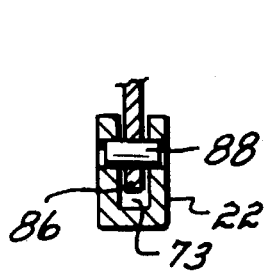
FIG. 5 is a cross-sectional view taken at lines 5—5 of FIG. 1.

As shown in FIG. 5, the handle element 22 has a generally C-shaped cross-sectional configuration providing a central cavity or slot 73 (although not shown, handle element 21 is similarly shaped). The handle elements 21 and 22 are attached to the needle holder 11 by a collar 75. Collar 75 encircles the midsection 63 of the plug 50 and includes opposed bifurcated tabs 76 and 77 which each include a central hole. The ends 71 and 72 of handle elements 21 and 22 are pivotally attached to these tabs with pins 78 and 79.

Handle elements 21 and 22 are also attached to the needle holder by linkage 23. Linkage 23 includes two generally "L" shaped links 81 and 82. The links 81 and 82 are mirror image, each include a long arm 83 and a short arm 84. The short arm 84 is bent at about a 52° angle relative to the long arm 83. The ends 85 and 86 of links 81 and 82 are pivotally attached with pins 87 and 88 to the handle elements 21 and 22.

Ends 91 and 92 of links 81 and 82 are pivotally attached by pin 93 to a pair of ears 94 (only one of which is shown) of cap 19 permitting rotation of the linkages relative to the handles and the cap. Cap 19 further includes a cylindrical wall 98 which surrounds spring 20 which in turn engages an end surface 101 of plug 50. Spring 20 is shown as a Bellville washer. However, other springs such as a spring washer can also be used.

Figure 3:
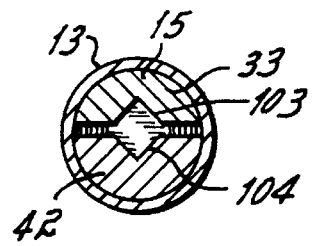
FIG. 3 is a cross-sectional view taken at lines 3—3 of FIG. 1.
Figure 4:
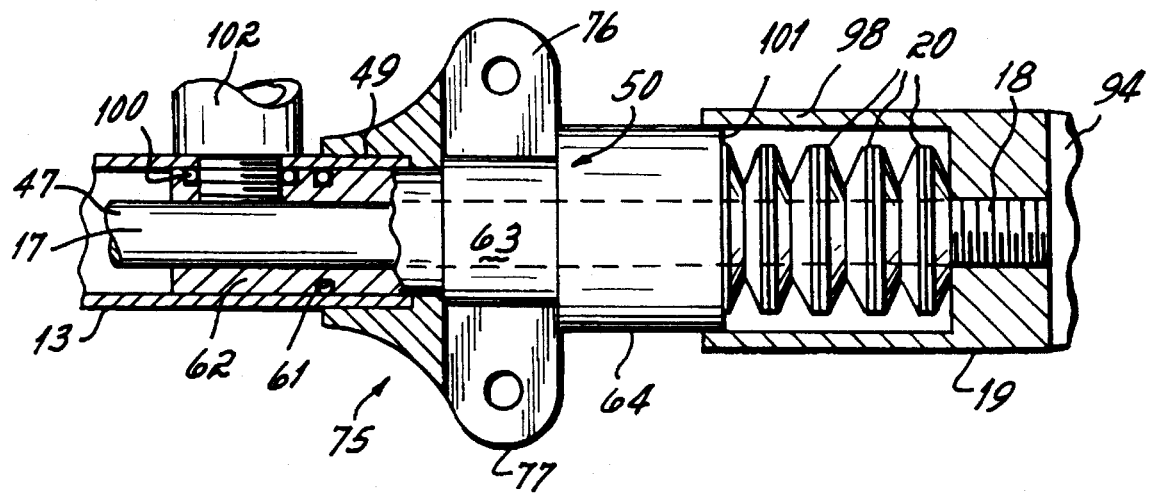
FIG. 4 is an enlarged view of the rear portion of the body of the present invention partially in cross section.

Finally, the needle holder includes a flush port 102 or lower lock which extends through the tubular body 13 and fixes or screws onto a threaded hole through innermost portion 62 of plug 50. An O-ring 100 between the plug 50 and the body wall 13 maintains a fluid tight seal. This permits fluid to enter through the port into the plug 50 and into body 13 toward the jaw pair 14. The threaded portion 43 of movable jaw element 16 is narrower than the internal diameter of the body 13. This allows fluid to flow around the threaded portion. A shown in FIG. 3, both of the fixed and stationary jaw elements 15 and 16 include central axial grooves 103 and 104 which provides a fluid path from the flush port 102 through the body 13 through jaw elements 15 and 16 to the exterior of the device. The flush port can alternatively be fixed to and extend through the collar 75, if desired.

According to the present invention, the needle holder in its natural state will be spring biased in a closed position with the jaw faces engaged biased towards each other by spring 20 which is a series of Belleville washers. When the handle elements 21 and 22 are squeezed the linkage 23 will force the ends 91 and 92 of the long arms of the links toward the cap 19. The pivot pin 93 will force the rod 17 downward, overcoming the compressive force of the spring 20. This will open the jaw elements by moving jaw 16 away from fixed jaw 15. By releasing the handles, the spring 20 will force the rod 17 in the opposite direction, forcing moveable jaw element 16 back against stationary jaw element 15.

Once used, the device is washed by forcing a disinfecting solution through flow port 102. This will clean the interior of the device. This can then be autoclaved.

Figure 6:
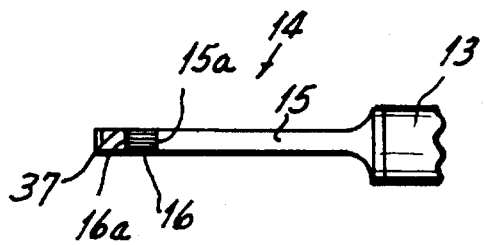
FIG. 6 is a view as seen along line 6—6 of FIG. 2 showing one embodiment for the jaw faces in an open position.
Figure 7:
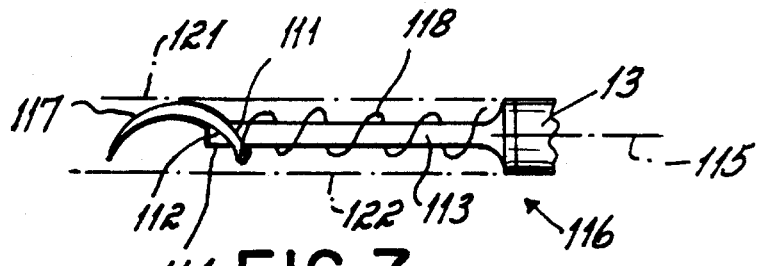
FIG. 7 is a view similar to FIG. 6 illustrating alternate jaw faces, the jaws being closed upon a needle.

In an alternate embodiment of the present invention shown in FIG. 6, jaw faces 111 and 112 of the stationary and moveable jaw elements 113 and 114 are at approximately a 60° angle relative to the axis 115 of the needle holder 116. The combined diameter of the jaw elements is less than the diameter of the central tube 13. This permits a needle 117 to be grasped by the needle holder with the thread 118 encircling the narrow portions of fixed and moveable jaw elements 113 and 114. As shown by dashed lines 121 and 122, the needle 117 does not extend beyond the exterior diameter of the central tube 13. Thus, the holder 116 with the needle 117 and thread 118 can be inserted through a cannula into the operative site in a laparoscopic procedure. This eliminates the need to place the needle into the operative site with one surgical tool and subsequently insert the needle holder.

The needle holder of the present invention provides numerous advantages. In addition to the ability to load the needle holder prior to insertion through the cannula, this device is spring biased in a closed position which enables the surgeon to hold the needle without pressing down on the handles. This relieves strain on the surgeon. Also, since the surfaces of the jaw elements directly engage each other so that substantially the entire jaw element of the fixed jaw engages the entire jaw surface of the stationary jaw element, there is a greater surface area of engagement which permits the needle to be grasped along the flat plane of the needle, This prevents rotation of the needle in use, And, of course most importantly, the needle holder of the present invention is useful for laparoscopic procedures.

Further, the handle mechanism itself can be used with any surgical instrument which can be operated by a rod or wire running through a shaft to open or close (move) jaw elements. For example, this handle could be used to manipulate scissors, forceps, suturing assists and surgical staplers. The springs can be used to maintain jaws in an open or closed position. The spring can be altered to provide the desired tension for the various instruments.

This has been a description of the present invention along with the preferred embodiment of the present invention. However, the invention itself should be defined only by the appended claims wherein I claim:

1. An elongated scopic needle holder having a handle connected to a first end of an elongated shaft and a jaw mechanism at a second end of said shaft;

said jaw mechanism including a first jaw element having a first planar jaw face;

a second L-shaped jaw element having a second planar jaw face, said jaw elements moveable relative to each other, said jaw faces being parallel to each other and remaining parallel to each other during relative movement between said law elements;

a spring within said elongated shaft forcing said first and second jaw faces into engagement;

said handle adapted to force a linkage located between said handle and said elongated against said spring as said handle is squeezed to thereby compress said spring and separate said jaw faces.

2. The needle holder claimed in claim 1 wherein each of said jaw faces has a planar surface;

wherein an angle is established between said surfaces of said jaw faces and wherein said angle is from about 30° to about 75° and wherein a diameter of said needle holder at said jaw elements is less than a diameter of said shaft, permitting a needle to be held between said jaw faces and be inserted through a trocar having an internal diameter about equal to the diameter of said shaft.

3. The needle holder claimed in claim 2 wherein said angle is about 60°.

4. The needle holder claimed in claim 1 wherein said second jaw element is connected to a rod passing through said shaft wherein said spring engages an end of said rod opposite said second jaw element forcing said second jaw face against said first jaw face.

5. The needle holder claimed in claim 4 wherein said handle includes a V-shaped linkage having first and second legs joined at a hinged portion wherein ends of said legs opposite said hinged portion pivotally engage first and second handle members wherein squeezing said handle members forces said legs towards each other and said hinged portion against said spring compressing said spring and opening said jaw.

6. The needle holder claimed in claim 1 wherein said shaft is a tubular body extending from a rear portion of said needle holder to said jaw elements;

a flush port extends through said tubular body near said handle portion;

said tube body providing a conduit from said flush port to said jaw elements;

a channel extending through said jaw elements to an opposite end of said needle holder.

7. The needle holder claimed in claim 6 wherein said rod extends through said shaft and wherein said spring is mounted exterior of said shaft, said spring held in potential compression and wherein compression of said handle acts to further compress said spring and thereby open said jaw elements.

8. The needle holder claimed in claim 1 including:

a rod extending through said shaft engaged at one end by said spring and at a second end by said moveable jaw element;

said handle acting to move said rod and thereby move said moveable jaw element.

9. A needle holder claimed in claim 1 wherein said jaw elements have cross-sections smaller than a cross-section of said shaft thereby permitting a needle to be held by said jaw elements and inserted through a cannula having a cross-section approximately equal to the cross-section of said shaft.

10. A surgical needle holder comprising:

a central tube and a first member and a second member which are slidably interconnected, said members extend beyond an end of said central tube, each of said members having a leading end and a trailing end;

a first jaw integral with the leading end of said first member and a second jaw integral with the leading end of said second member, each of said jaws having a gripping surface and said gripping surfaces opposing each other and being generally parallel to each other wherein said needle holder has an elongated axis and wherein the plane of said jaw elements forms an angle with said axis, said angle being from about 30° to about 75°;

a handle attached to said central tube, said handle operable to move said jaw elements relative to each other;

said tube having a first diameter and said first and second members having a combined diameter which is narrower than said first diameter permitting a curved needle to be held between said jaw faces without extending beyond the first diameter.

11. A surgical needle holder having a handle attached to a first end of an elongated tubular body portion;

first and second jaw elements mounted at a second end of said tubular element;

a spring in said tubular body portion means forcing said jaw elements towards each other in an engaging relationship;

a linkage between said handle and said tubular body acting to compress said spring means when said handle is squeezed, thereby separating said jaw elements;

a flush port extending into said tubular body portion;

said jaw elements having a channel extending therethrough whereby fluid inserted in said flush port may flow through said body portion and out through said channel.

* * * * *